United States Patent [19]
Dou et al.

[11] Patent Number: 5,741,660
[45] Date of Patent: Apr. 21, 1998

[54] METHOD OF MEASURING ENZYME REACTION BY RAMAN SCATTERING

[75] Inventors: Xiaoming Dou; Yutaka Yamasaki; Harumi Uenoyama; Yoshinori Yamaguchi, all of Kyoto, Japan

[73] Assignee: Kyoto Dai-ichi Kagaku Co., Ltd., Minami-ku, Japan

[21] Appl. No.: 594,205

[22] Filed: Jan. 30, 1996

[30] Foreign Application Priority Data

Feb. 1, 1995 [JP] Japan .................................. 7-037564

[51] Int. Cl.$^6$ .................................................. C12Q 1/26
[52] U.S. Cl. .................................................. 435/25; 435/4
[58] Field of Search ........................... 435/25, 7.93, 7.94, 435/7.95, 4; 436/164, 173, 518, 525; 250/341.1

[56] References Cited

U.S. PATENT DOCUMENTS

| | | |
|---|---|---|
| 5,266,498 | 11/1993 | Tarcha et al. . |
| 5,376,556 | 12/1994 | Tarcha et al. . |
| 5,481,113 | 1/1996 | Dou et al. ........................... 250/341.1 |

OTHER PUBLICATIONS

Kitagawa et at (J. Biochem, vol. 84, No. 5, 1978, pp. 1245–1252).
"Resonance Raman Studies of Cytochrome Oxidase".
Adar et al (Biochimica et Biophysica Acta, vol. 502, 1978, pp. 80–86), Resonance Raman Spectra of Cytochrome Oxidase Evidence for Photoreduction by Laser Photons in Resonance with the Soret Band.

*Primary Examiner*—John Kight
*Assistant Examiner*—Dameron Jones
*Attorney, Agent, or Firm*—Nikaido Marmelstein Murray & Oram LLP

[57] ABSTRACT

As to reaction solutions in which the amount of each potassium ferricyanate, glucose oxidase and glucose substrate are set at a constant value while glucose concentrations are varied, intensity changes of peaks at a shift wavenumber of 2081 cm$^{-1}$ in light scattering spectra are measured every 10 seconds, the maximum values of the intensity changes of the peaks at the respective glucose concentrations obtained, for obtaining a calibration curve from correlations between the maximum values of the reaction velocities and the glucose concentrations. The calibration curve is employed for carrying out quantitative measurement of an unknown sample.

9 Claims, 8 Drawing Sheets

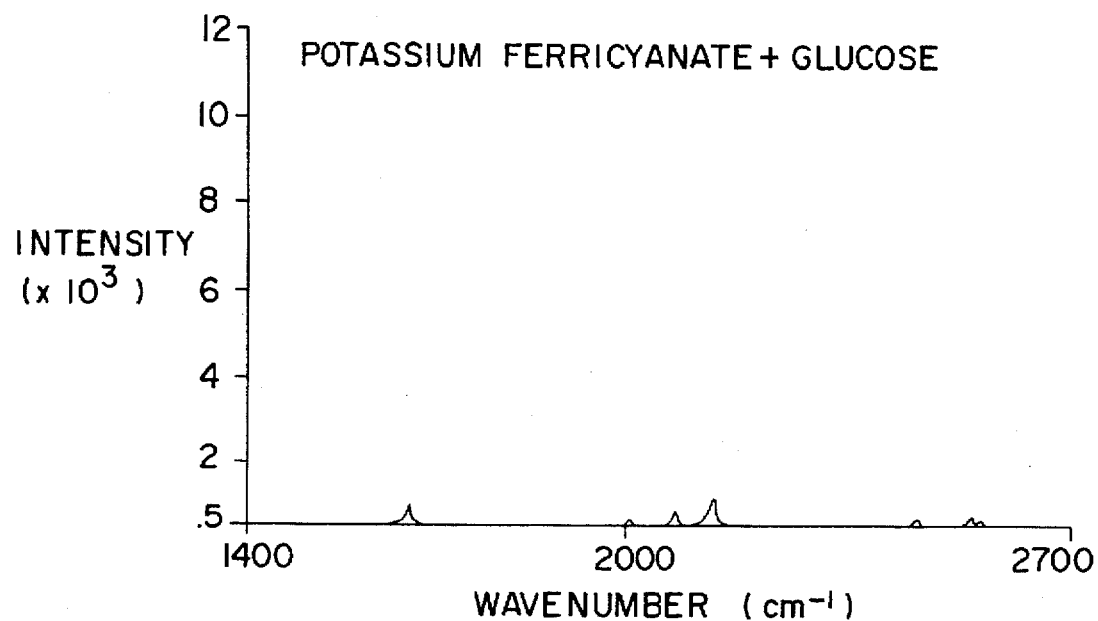
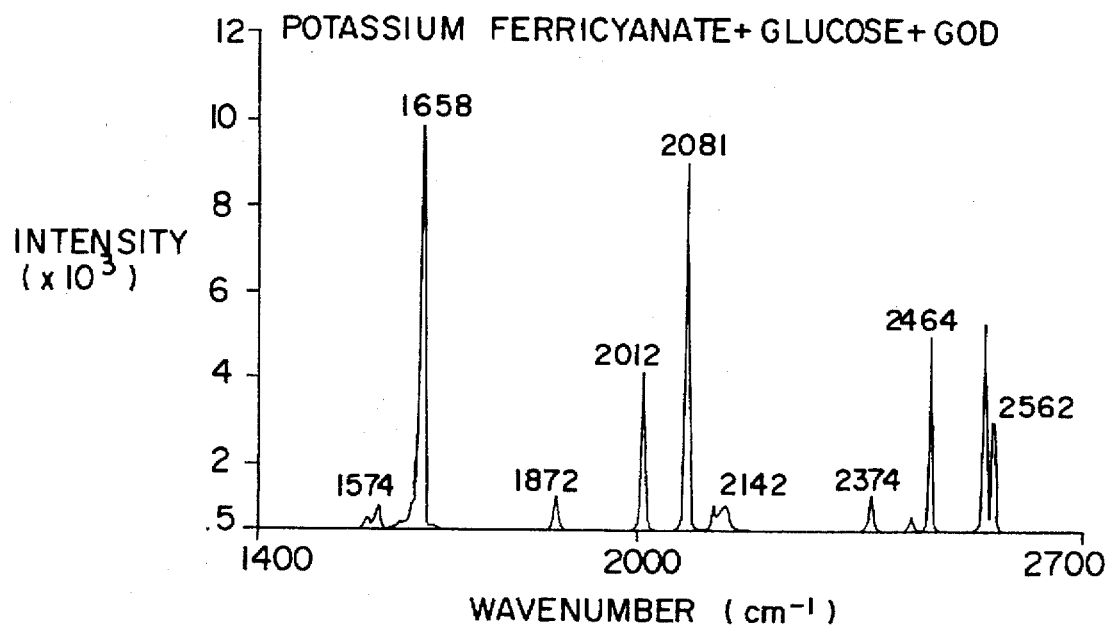

METHOD OF MEASURING ENZYME REACTION BY RAMAN SCATTERING

BACKGROUND OF THE INVENTION

1. Field of the Invention

The present invention relates to qualitative measurement and quantitative measurement of a target substrate of a specific enzyme in an enzyme reaction, and a method of measuring activity of an enzyme.

2. Description of the Background Art

Some methods are carried out as methods of measuring an enzyme reaction, and the following methods are known in the art, if the enzyme reaction is a reaction system generating hydrogen peroxide, for example:

(1) A method employing a hydrogen peroxide electrode.

This method is adapted to measure current change which is caused when hydrogen peroxide is electrically oxidized, and hence an influence is exerted by a reducing substance coexisting in the sample solution.

(2) Leuco or oxidation condensation type spectrophotometry (refer to Japanese Patent Laying-Open Gazette No. 59-182361 (1984)), which is typically adapted to react hydrogen peroxide with 4-aminoantipyrin and phenol for coloring, and to measure absorption of the coloring reaction solution at 505 nm. In the leuco type spectrophotometry, an error is readily caused by coloring of a reagent blank resulting from natural oxidation of a chromogen. In the oxidation condensation type spectrophotometry, on the other hand, a negative error is readily caused by a reducing substance. Further, hydrogen peroxide of 2 moles is required for forming a pigment of 1 mole, and hence this method is unsuitable for determination of a component of a small quantity.

(3) A fluorescent method, which is adapted to react hydrogen peroxide with homovanillic acid to generate fluorescence, and to measure the fluorescence. In the fluorescent method, sensitivity remarkably depends on the performance of an apparatus. Thus, this method is extremely influenced by a temperature and a coexisting substance.

(4) Chemiluminescence, which is adapted to excite a substrate of luminol or lucigenin through oxidizing power of hydrogen peroxide under presence of a catalyst such as POD (peroxidase) and to detect light generated when the substrate returns from the excited state to the ground state. In the chemiluminescence, a sufficient quantity of light emission is obtained only under alkaline conditions. The reaction velocity is slow and reproducibility is insufficient. Further, light emission intensity is reduced upon coexistence of protein.

On the other hand, a method called Raman scattering analysis is included in optical analysis methods. This Raman scattering analysis method utilizes the following phenomenon: When specific molecules are irradiated with radiation energy which is in the form of electromagnetic waves, small parts of molecules holding photons do not return to original vibration levels but fall to those having different electron ground states after releasing the held photons. Therefore, levels of energy released from these molecules are specific thereto, and the specific molecules can be identified by detecting the levels of the released energy as electromagnetic waves.

While an energy beam which is released by Raman scattering may be in a state lower than absorbed energy (stokes Raman scattering) or higher than the same (anti-stokes Raman scattering), the intensity of anti-stokes Raman scattering is extremely weak since the number of electrons which are in excited states is by far smaller than that of electrons which are in ground states. Thus, the method of identifying specific molecules generally employs measurement by stoke Raman scattering.

There has been reported no example of measuring an enzyme reaction through Raman scattering.

SUMMARY OF THE INVENTION

An object of the present invention is to enable qualitative measurement or quantitative measurement of a substrate of an enzyme reaction, or measurement of activity of an enzyme.

In measurement of Raman scattering of ferricyanic ions performed by the inventors, only extremely weak Raman scattering was observed when a sample solution containing a target substrate of a certain enzyme and ferricyanic ions was irradiated with an excitation beam of a single wavelength. However, the inventors have discovered such a phenomenon that some peaks of a Raman scattering spectrum from the sample solution before addition of the enzyme are reinforced with progress of an enzyme reaction when the enzyme is added to the sample solution to cause an enzyme reaction, to carry out qualitative measurement, quantitative measurement or enzymatic activity measurement of the enzyme reaction through the reinforced Raman scattering peaks.

In a qualitative measuring method according to the present invention for measuring presence or absence of a target substrate of an enzyme, the enzyme is added to a sample solution to which ferricyanic ions are added, the sample solution is irradiated with an excitation beam of a single wavelength before and after the addition of the enzyme so that scattered light from the sample solution is received and separated into its spectral components, and presence or absence of the target substrate of the enzyme is measured depending on whether or not the Raman scattering spectrum from the sample solution after the addition of the enzyme includes reinforced peaks of those of the Raman scattering spectrum from the sample solution before the addition of the enzyme.

In a quantitative measurement method according to the present invention for obtaining substrate concentration, operations of adding ferricyanic ions of constant concentrations and enzymes of constant units to standard sample solutions containing target substrates having known concentrations for causing an enzyme reaction, irradiating the standard sample solutions with excitation beams of single wavelength for receiving scattered light from the standard sample solutions and separating the scattered light into spectral components, and measuring reaction velocities from time changes of peak intensity values of reinforced peaks of those of Raman scattering spectra from the standard sample solutions on a plurality of standard sample solutions having different target substrate concentrations for forming a calibration curve showing relations between the target substrate concentrations and the reaction velocities. Ferricyanic ions and an enzyme of the same concentration and the same unit as those in the measurement for forming the calibration curve are added to a measurement sample solution containing a target substrate having an unknown concentration, and this measurement sample solution is irradiated with an excitation beam similarly to the above for measuring a reaction velocity from time changes of peak intensity values of the same Raman scattering peaks as those employed for forming the calibration curve, thereby obtaining the substrate concentration of the measurement sample solution on the basis of the calibration curve.

In an enzymatic activity measuring method according to the present invention for obtaining activity of an enzyme, ferricyanic ions of a constant concentration and an enzyme of a constant unit are added to a sample solution containing a target substrate having a known concentration for causing an enzyme reaction, the sample solution is irradiated with an excitation beam of a single wavelength so that scattered light from the standard sample solution is received and separated into its spectral components, and a reaction velocity is measured from time changes of peak intensity of reinforced peaks of those of a Raman scattering spectrum from the sample solution before the enzyme reaction, thereby obtaining activity of the enzyme on the basis of the reaction velocity.

FIG. 1A and FIG. 1B shows changes of Raman scattering spectra of ferricyanic ions in enzyme reaction systems having substrates of glucose and enzymes of glucose oxidase. FIG. 1A shows the Raman spectrum of ferricyanic ions measured by adding the ferricyanic ions to a reaction solution containing glucose. In this reaction system, only extremely weak Raman scattering of the ferricyanic ions is observed.

On the other hand, FIG. 1B shows a Raman scattering spectrum which was measured after several minutes from addition of glucose oxidase (GOD), serving as an enzyme, to the reaction solution of FIG. 1A containing glucose and ferricyanic ions. This spectrum includes some peaks, in which some peaks observed in the Raman scattering spectrum from the reaction solution before the addition of the enzyme were reinforced.

FIG. 2A and FIG. 2B shows changes of Raman scattering spectra of ferricyanic ions in other enzyme reaction systems. In FIG. 2A showing a result of an operation of adding ferricyanic ions to a reaction solution containing lactate as a substrate and measuring its Raman scattering spectrum, weak Raman scattering peaks of the ferricyanic ions are observed similarly to FIG. 1A.

On the other hand, FIG. 2B shows a Raman scattering spectrum which was obtained by adding lactate oxidase (LOD) as an enzyme to the reaction solution of FIG. 2A containing lactate and ferricyanic ions and making measurement after a lapse of several minutes. This Raman scattering spectrum also includes peaks in which some peaks observed in the Raman scattering spectrum from the reaction solution before the addition of the enzyme were reinforced.

Comparing the spectra of FIG. 1B and FIG. 2B with each other, the reinforced Raman scattering peaks appear at the same shift wavenumbers to indicate that the peaks of these spectra are Raman scattering spectra by the same substance, although the enzyme reaction systems are different from each other. It is understood that the same influences are exerted regardless of the types of the enzyme reactions, although it is not clarified how the ferricyanic ions are influenced by progress of the enzyme reactions. The Raman scattering peaks in which the ferricyanic ions are influenced by the enzyme reactions and the peak intensity levels are reinforced are present at 1550 to 1680 cm$^{-1}$, 1850 to 1880 cm$^{-1}$, 2000 to 2150 cm$^{-1}$, 2350 to 2380 cm$^{-1}$ and 2450 to 2580 cm$^{-1}$ in shift wavenumbers with respect to excitation wavelengths. Concrete examples of the peak positions are 1574 cm$^{-1}$, 1658 cm$^{-1}$, 1872 cm$^{-1}$, 2012 cm$^{-1}$, 2081 cm$^{-1}$, 2142 cm$^{-1}$, 2374 cm$^{-1}$, 2464 cm$^{-1}$, 2562 cm$^{-1}$ and the like.

According to the present invention, qualitative measurement is performed on the fact that an enzyme reaction is caused by reinforcement of these Raman scattering peaks, i.e., the fact that the target substrate of the enzyme is present in the sample solution, and quantitative measurement is performed through any of these Raman scattering peaks. Further, the activity of the enzyme is measured by measuring the velocity for reinforcing any of these peaks.

An enzyme has substrate specificity and reaction specificity causing only a certain reaction with respect to a specific substance (target substrate). When an enzyme reaction is caused, its reaction product progresses at a constant velocity in an initial stage of the reaction, and thereafter the reaction velocity is gradually reduced, in a state concretely illustrated in FIG. 4 described later as Example. A reaction of the following equation (1), which is known as the Michaelis-Menten equation, holds between a reaction velocity vo (the maximum value of the reaction velocity) and a substrate concentration [S] in an initial stage of an enzyme reaction:

$$vo=(Vmax \cdot [S])/([S]+Km) \qquad (1)$$

where Vmax represents the maximum reaction velocity and Km is called the Michaelis constant, and FIG. 3(A) shows this.

The Michaelis constant Km is a value corresponding to the substrate concentration [S] obtained when the reaction velocity vo is Vmax/2, and the maximum reaction velocity Vmax and the Michaelis constant Km provide activity of the enzyme.

It is possible to draw the graph shown in FIG. 3(A) for estimating the maximum reaction velocity Vmax and obtaining the Michaelis constant Km by changing the substrate concentration [S] while making the enzyme concentration constant and measuring the reaction velocity vo.

The maximum reaction velocity Vmax, which is an asymptotic value, cannot be correctly obtained from the graph of FIG. 3A. As a method of experimentally obtaining the Michaelis constant Km, known is a method employing the Lineweaver-Burk plot. Both sides of the equation (1) are reversed as follows:

$$1/vo=(Km/Vmax)(1/[S])+(1/Vmax) \qquad (2)$$

The equation (2) can be expressed in the form of a linear expression as shown in FIG. 3B with 1/[S] and 1/vo on the axes of abscissas and ordinates, whereby Km and Vmax can be experimentally obtained by expressing Vo obtained by an experiment in the graph of FIG. 3B with respect to the substrate concentration [S].

According to the present invention, as hereinabove described, ferricyanic ions are added to an enzyme reaction system for obtaining the maximum value vo of increase velocities of Raman scattering peaks which are reinforced since the ferricyanic ions are influenced by an enzyme reaction, so that activity of the enzyme can be obtained on the basis of the equation (1) or (2) between the maximum value vo and the substrate concentration [S].

The enzyme reaction to which the present invention is not restricted to that illustrated above. The present invention is also applicable to enzyme reactions by oxidoreductases such as pyranose oxidase, bilirubin oxidase, cholesterol oxidase and polyphenol oxidase, and those of other types of enzymes, for example.

According to the present invention, qualitative measurement or quantitative measurement of a substrate, or enzymatic activity measurement is performed by measuring Raman scattered light which is reinforced through ferricyanic ions influenced by an enzyme reaction, whereby an enzyme reaction can be measured by a simple optical measuring method.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1A and FIG. 1B illustrate Raman scattering spectra from ferricyanic ions in glucose/glucose oxidase reaction systems before and after enzyme reactions respectively;

DESCRIPTION OF THE PREFERRED EMBODIMENTS

250 μl of a glucose solution (100 mg/dl) serving as a substrate, 14.5 U of glucose oxidase serving as an enzyme and 250 μl of a potassium ferricyanate solution (0.5M) are introduced into a quartz scattered light cell and adjusted with a phosphoric acid buffer solution to be pH 7.4 for preparing a sample solution, which in turn is maintained at 25° C. and reacted. An He-Ne laser beam is incident upon the reaction solution as an excitation beam, and scattered light thereof is separated into its spectral components for measuring growth of a peak at a position shifted by a wavenumber of 2081 $cm^{-1}$ from the wavelength of the excitation beam every 10 seconds. The result is shown in FIG. 4 as symbol "a".

When the reaction is started, the peak intensity is substantially linearly increased in the initial stage, and thereafter the increased velocity is reduced. The reaction velocity vo at which the peak intensity is linearly increased in the initial stage is measured.

Figure 2A:
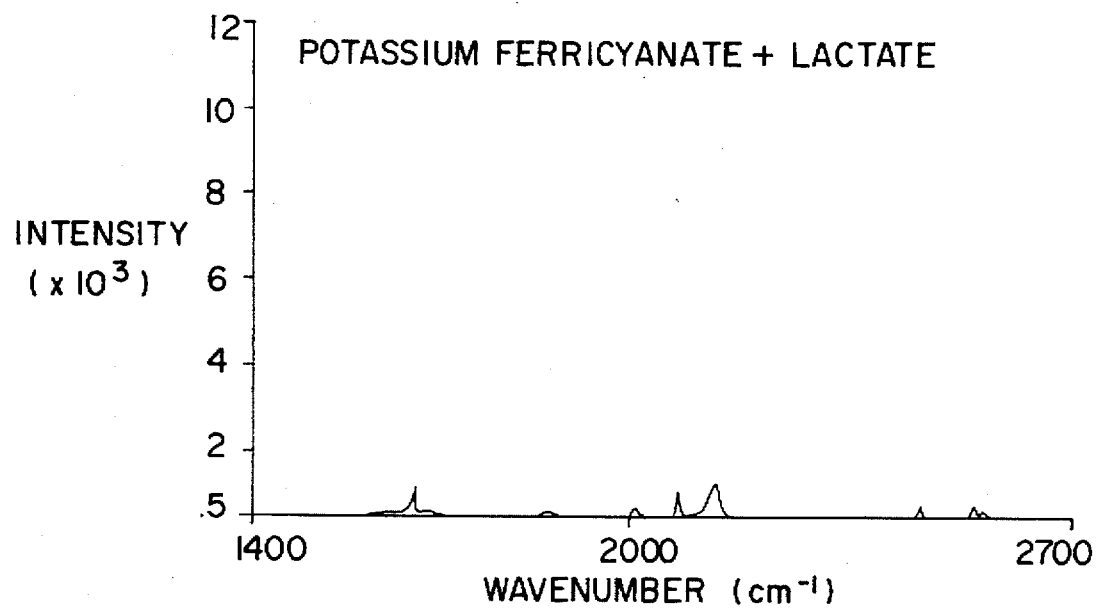
FIG. 2A and FIG. 2B illustrate Raman scattering spectra from ferricyanic ions in lactate/lactate oxidase reaction systems before and after enzyme reactions respectively.
Figure 2B:
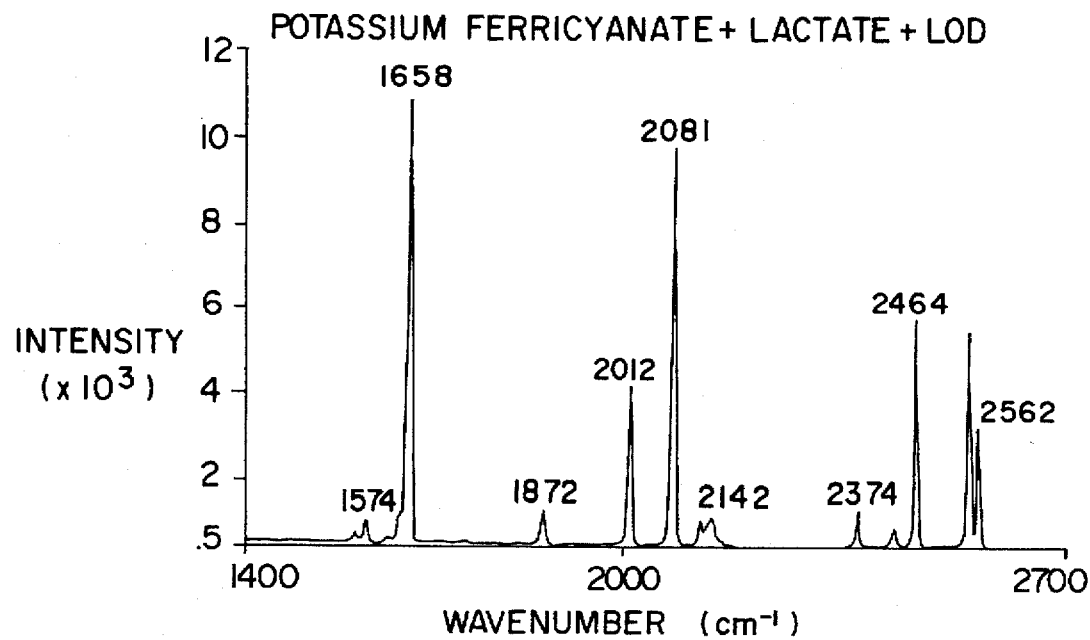
Figure 3A:
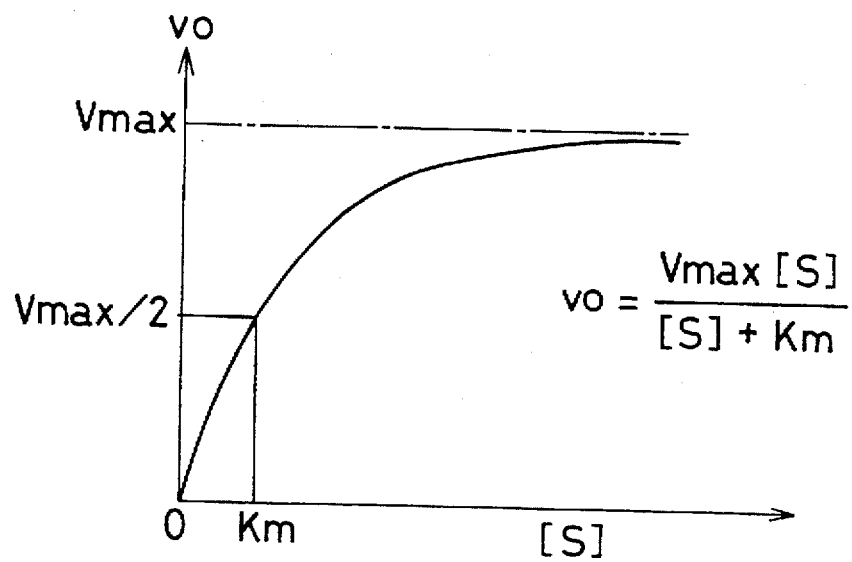
FIG. 3A and FIG. 3B show the Michaelis-Menten equation and the Lineweaver-Burk plot respectively in relation to enzyme reaction velocities.
Figure 3B:
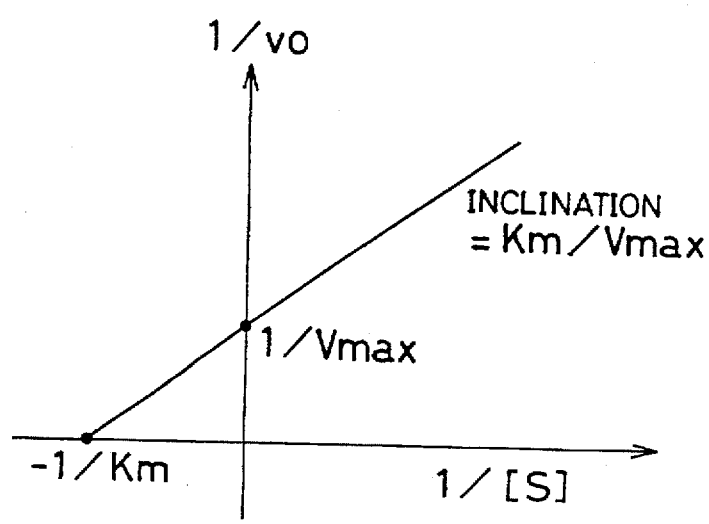
Figure 4:
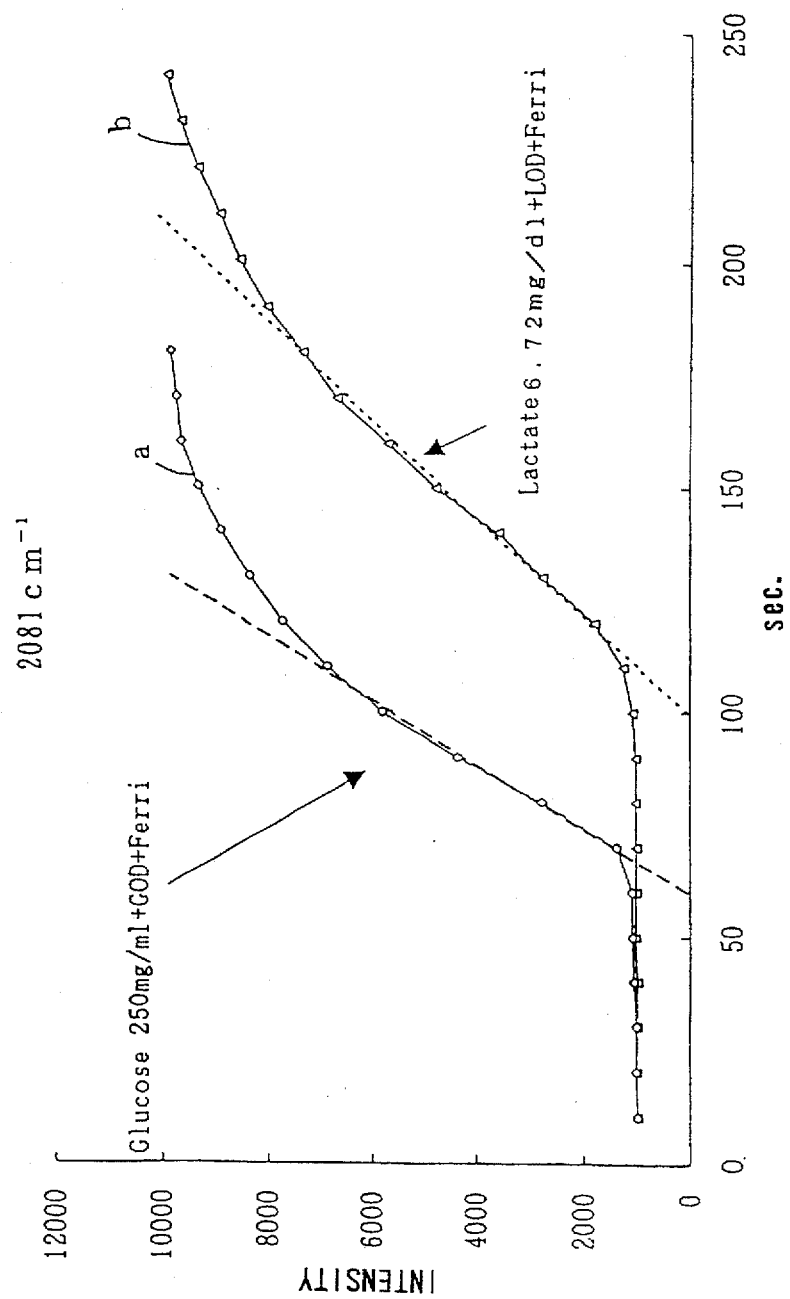
FIG. 4 illustrates time changes of peaks at a shift wavenumber of 2081 $cm^{-1}$ reinforced by enzyme reactions.

Similarly, FIG. 4 shows a result obtained by adding potassium ferricyanate to a reaction system of substrate lactate and enzyme lactate oxidase for causing a reaction and measuring a change of the same peak at the shift wavenumber of 2081 $cm^{-1}$ as symbol "b".

Figure 5:
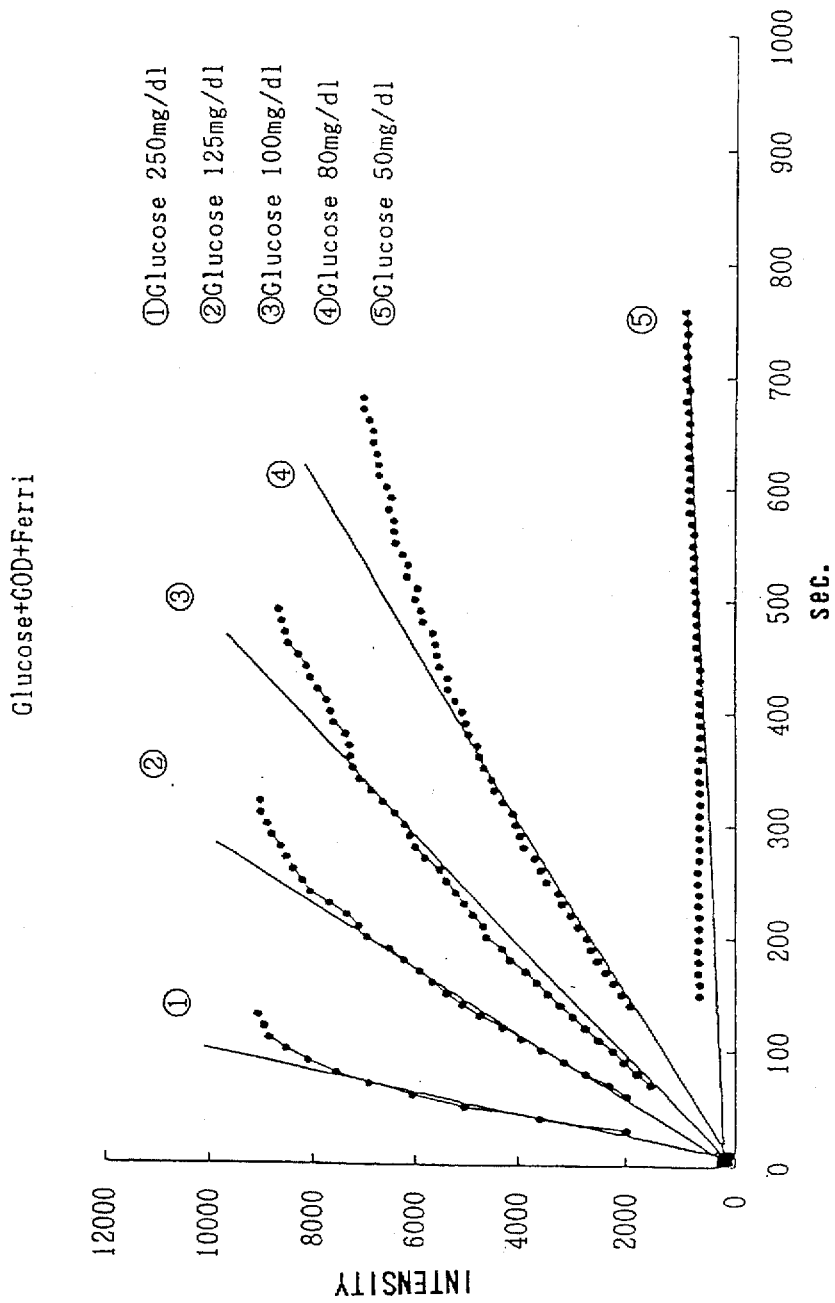
FIG. 5 illustrates time changes of peaks at a shift wavenumber of 2081 $cm^{-1}$ as to standard sample solutions having various glucose concentrations.

As to reaction solutions in which the amount of each potassium ferricyanate solution (0.5M) is set at a constant value of 250 μl, the concentration of each glucose oxidase is set at a constant value of 14.5 U and the amount of each glucose substrate is set at a constant value of 250 μl while glucose concentrations are varied as 250 mg/dl, 125 mg/dl, 100 mg/dl, 80 mg/dl and 50 mg/dl, FIG. 5 shows results obtained by measuring intensity changes of peaks at the shift wavenumber of 2081 $cm^{-1}$ in light scattering spectra every 10 seconds.

Figure 6:
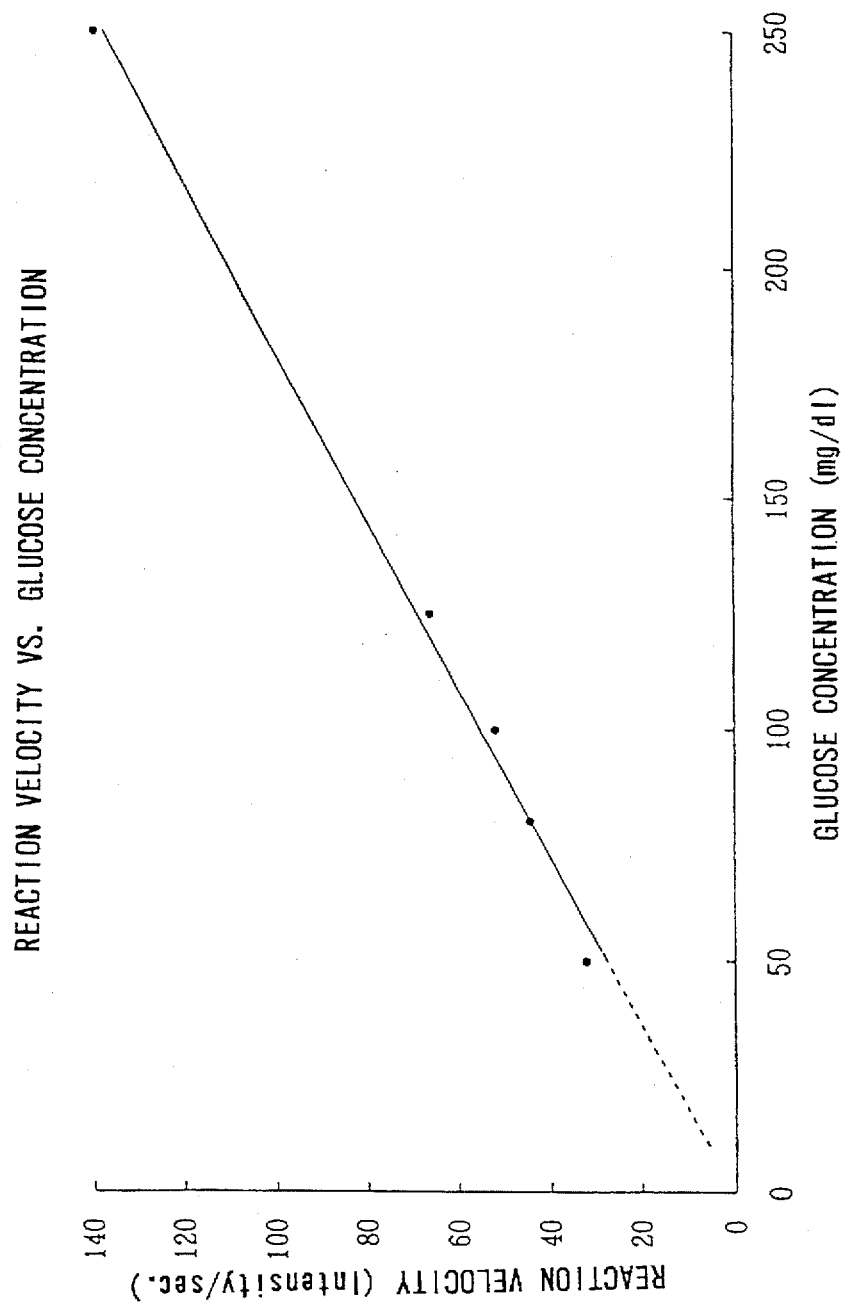
FIG. 6 shows a calibration curve of glucose concentrations formed on the basis of the results of measurement shown in FIG. 5.

FIG. 6 shows results of correlations between maximum values of reaction velocities at the respective glucose concentrations obtained from the results of FIG. 5 and the glucose concentrations. FIG. 6 serves as a calibration curve for obtaining an unknown glucose concentration of a measurement sample solution.

In order to carry out quantitative measurement of a measurement sample having an unknown glucose concentration, 250 μl of a potassium ferricyanate solution (0.5M) and 14.5 U of glucose oxidase are added to 250 μl of the measurement sample solution similarly to the case of forming the calibration curve, the mixture is adjusted to pH 7.4, and the sample temperature is maintained at 25° C. so that the maximum value of the reaction velocity is measured from an intensity change of a prescribed peak, such as the peak at the shift wavenumber of 2081 $cm^{-1}$, for example. The glucose concentration of the substrate can be obtained by applying the measured maximum value of the reaction velocity to the calibration curve of FIG. 6.

Figure 7:
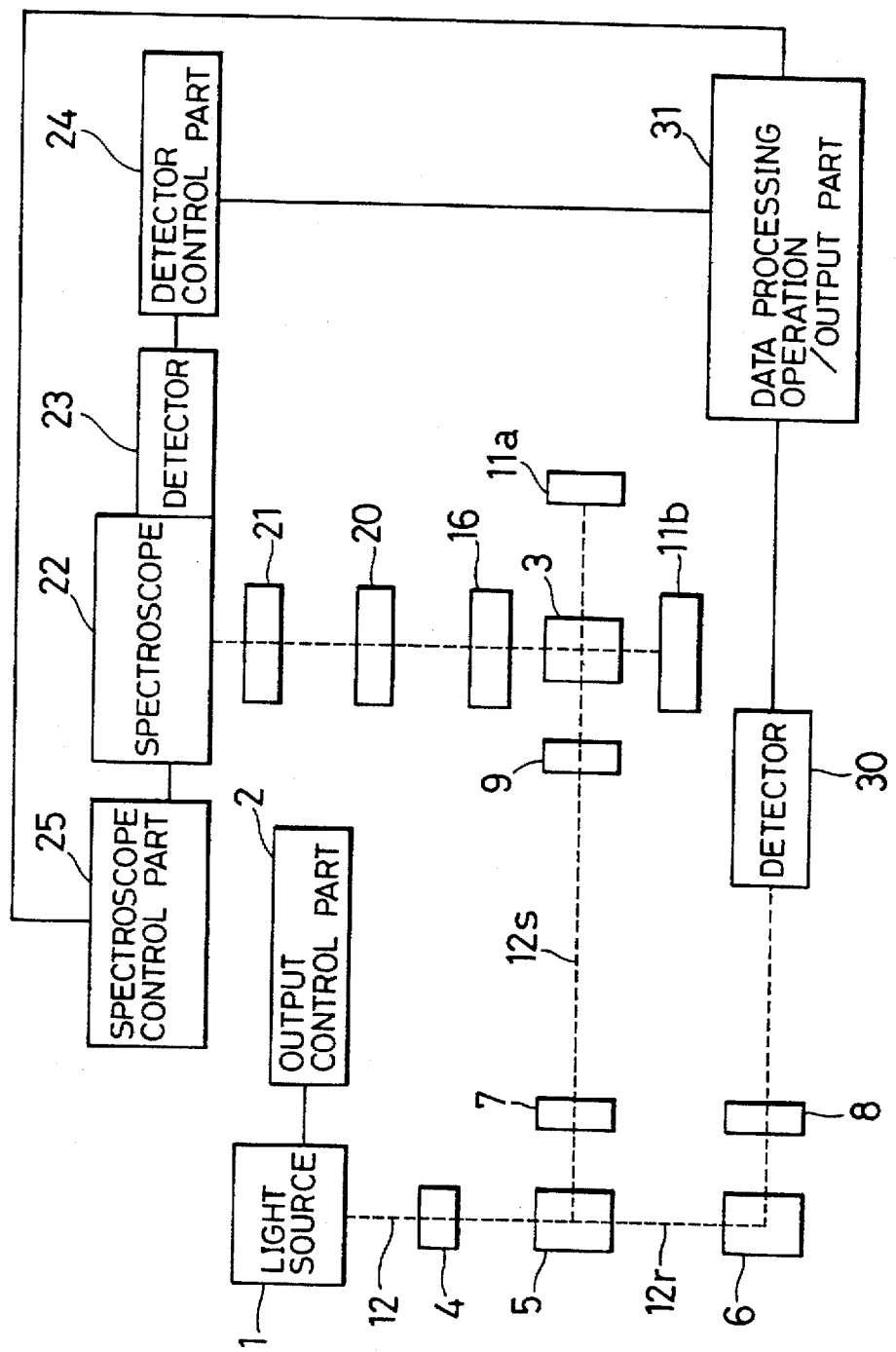
FIG. 7 is a block diagram showing an exemplary measuring apparatus for carrying out the present invention.

FIG. 7 illustrates an exemplary apparatus for measuring Raman scattered light in the present invention. Numeral 1 denotes an excitation light source, which is formed by a laser unit, for example, for measuring Raman scattered light. The laser unit, which can be prepared from an Ar ion laser, a Kr ion laser, an He-Ne laser, an He-Cd laser or an Nd:YAG laser performing continuous oscillation, or a pulse laser, can be selected from lasers of wide wavelength ranges over near ultraviolet and near infrared regions. A halogen lamp or the like can also be employed as a light source other than the laser unit. It is assumed here that an He-Ne laser is employed as the light source 1. Numeral 2 denotes a power source unit controlling the output of the light source 1.

Numeral 4 denotes a bandpass filter, which is adapted to cut a sideband from a laser beam 12 oscillated from the light source 1. The laser beam 12 is separated into an excitation beam 12s of a sample side and a reference beam 12r of a reference side, so that the excitation beam 12s is converged and incident upon a cell 3 by a lens 9 through a bandpass filter 7 for cutting a wavelength beam which is generated by a half mirror 5.

The cell 3, which is a tubular scattered light cell of quartz, contains a reaction solution, and is maintained at a constant temperature of 25° C., for example. A mirror 11a is arranged in an incident direction of the excitation beam 12s in order to reinforce scattered light which is generated from the reaction solution contained in the cell 3, so that the excitation beam 12s is transmitted through the cell 3 and thereafter reflected by the mirror 11a to be incident upon the cell 3 again, thereby reinforcing Raman scattering. Another mirror 11b is arranged in a direction which is at 90° with respect to the incident direction of the excitation beam 12s for reflecting the same toward a spectroscope 22, so that the scattered light which is generated from the cell 3 is converged by converging lenses 16 and 20 with the excitation beam along with that reflected by the mirror 11b and converged by the spectroscope 22 through a filter 21. The filter 21 is adapted to cut an excitation light component for introducing only a scattered light component into the spectroscope 22. The spectroscope 22 and a detector 23 are formed by those of multi-channel detection systems by polychromators in which plural detection elements are arranged along the dispersion direction of the spectroscope 22. Numeral 24 denotes a detector control part for deriving an output from the multi-channel detector 23 every wavelength.

The spectroscope 22 can alternatively be prepared from a scan spectroscope while the detector 23 can be prepared by that comprising a single detection element. In this case, a spectroscope control part 25 is required for wavelength-scanning the spectroscope 22.

On the other hand, the reference beam 12r which is separated from the excitation beam 12s through the half mirror 5 is bent toward a detector 30 through a mirror 6, to be incident upon the detector 30 through a bandpass filter 8 for cutting a wavelength beam generated from the mirror 6, so that light source intensity is detected.

A data processing operation/output part 31 corrects a detected value of Raman scattered light by the spectroscope 22 and the detector 23 with a detected value of the reference beam side detector 30 indicating the light source intensity for obtaining a Raman scattering spectrum, thereby calculating the maximum value of the reaction velocity from an intensity change of a specific peak and outputting the same. When quantitative measurement is performed, the data processing operation/output part 31 holds calibration curve data which are formed by previous measurement, and calculates a substrate concentration from the maximum value of a reaction velocity obtained by measuring an unknown sample on the basis of the calibration curve for outputting the same. When the spectroscope 22 performs wavelength scanning, the data processing operation/output part 31 performs wavelength scanning through the spectroscope control part 25.

Figure 8A:
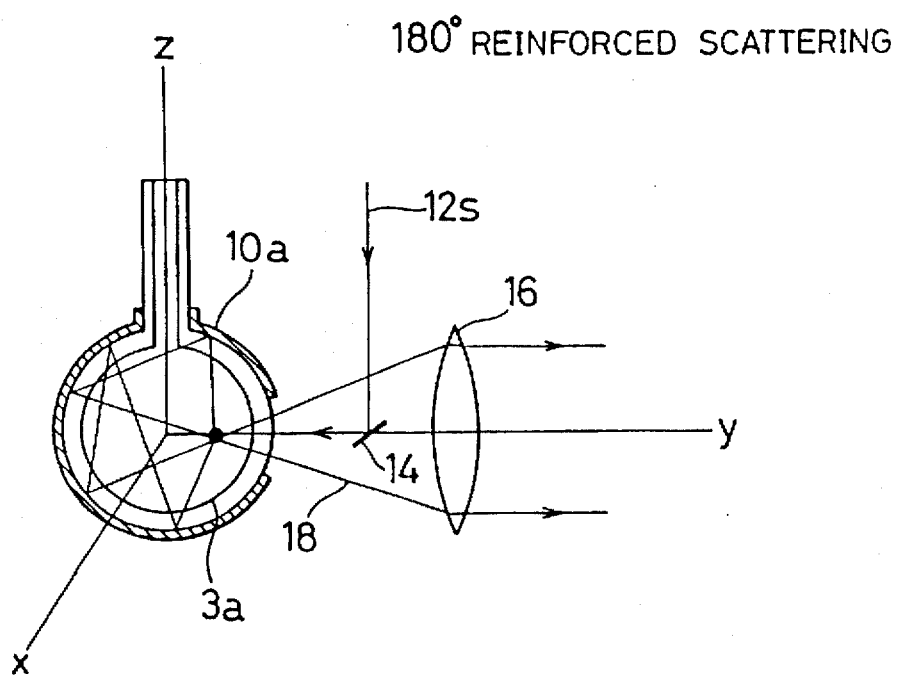
FIG. 8A and FIG. 8B are sectional views showing cell parts for extracting 180° reinforced scattering and 90° reinforced scattering respectively.
Figure 8B:
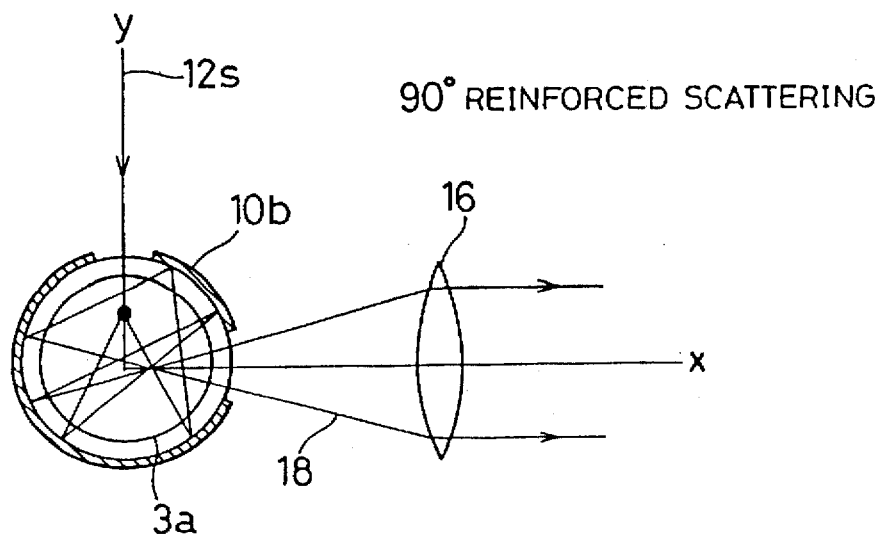

FIGS. 8A and 8B show exemplary cells for further effectively reinforcing Raman scattering by excitation beams.

Referring to FIG. 8A, a cell 3a is in the form of a round bottom flask which is made of a transparent material such as glass, quartz or polyethylene terephthalate, for storing a sample solution. This cell 3a is engaged in an integrating-spherical cell holder 10a. The cell holder 10a has a reflecting inner surface. The cell holder 10a is provided with a window for receiving an excitation beam 12s which is emitted from an excitation light source and extracting scattered light in a direction which is at an angle of 180° to the direction of incidence. The excitation beam 12s is bent by a mirror 14, and introduced into the cell 3a through the window of the cell holder 10a.

Numeral 16 denotes a condenser lens for condensing the scattered light outgoing from the window of the cell holder 10a. While the mirror 14 is arranged on an optical axis of the condenser lens 16, the same is sufficiently small as compared with the aperture of the condenser lens 16, and will not inhibit the condenser lens 16 from condensing the scattered light. The excitation beam which is applied to the sample solution stored in the cell 3a is repeatedly reflected by the inner surface of the cell holder 10a, extracted from the window of the cell holder 10a with Raman scattering, and guided toward a spectral detector.

Referring to FIG. 8B, on the other hand, a cell holder 10b is provided with windows for extracting scattered light in a direction which is at 90° with respect to the direction of incidence of an excitation beam 12s. The cell 3a is engaged in the integrating-spherical cell holder 10b having a reflecting inner surface, while the cell holder 10b is provided with windows for introducing the excitation beam 12s from a direction y and extracting scattered light 18 in a direction x which is at an angle of 90° to the direction y.

A plurality of peaks are recognized in Raman scattering in which ferricyanic ions are influenced by an enzyme reaction and reinforced, whereby qualitative measurement or quantitative measurement of a substrate, or enzymatic activity measurement can be carried out not only through the peak at the shift wavenumber 2081 $cm^{-1}$ employed in Example but through any other peak.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A qualitative measuring method comprising the steps of:

adding an enzyme to a sample solution to which ferricyanic ions are added;

irradiating said sample solution with an excitation beam of a single wavelength before and after said addition of said enzyme for receiving scattered light from said sample solution and separating said scattered light into its spectral components; and measuring presence or absence of a target substrate of said enzyme depending on whether or not a Raman scattering spectrum from said sample solution after said addition of said enzyme includes a reinforced peak of that of a Raman scattering spectrum from said sample solution before said addition of said enzyme.

2. The measuring method in accordance with claim 1, wherein a peak being present at 1550 to 1680 $cm^{-1}$, 1850 to 1880 $cm^{-1}$, 2000 to 2150 $cm^{-1}$, 2350 to 2380 $cm^{-1}$ or 2450 to 2580 $cm^{-1}$ in shift wavenumber with respect to an excitation wavelength is employed as a Raman scattering peak.

3. The measuring method in accordance with claim 1, wherein said enzyme is an oxidoreductase.

4. A quantitative measuring method comprising the steps of:

carrying out operations of adding ferricyanic ions of constant concentrations and enzymes of constant units to standard sample solutions containing target substrates having known concentrations for causing enzyme reactions, irradiating said standard sample solutions with excitation beams of single wavelengths for receiving scattered light from said standard sample solutions and separating said scattered light into spectral components, and measuring reaction velocities from time changes of peak intensity values of reinforced peaks of those of Raman scattering spectra from said standard sample solutions before enzyme reactions on a plurality of standard sample solutions having different target substrate concentrations for forming a calibration curve indicating relations between said target substrate concentrations and said reaction velocities; and adding ferricyanic ions and an enzyme of the same concentration and the same unit as those in said measurement for forming said calibration curve to a measurement sample solution containing a target substrate having an unknown concentration and irradiating said measurement sample solution with an excitation beam similarly to the above for measuring a reaction velocity from a time change of peak intensity of the same Raman scattering peak as those employed for forming said calibration curve, thereby obtaining a substrate concentration of said measurement sample solution on the basis of said calibration curve.

5. The measuring method in accordance with claim 4, wherein a peak being present at 1550 to 1680 $cm^{-1}$, 1850 to 1880 $cm^{-1}$, 2000 to 2150 $cm^{-1}$, 2350 to 2380 $cm^{-1}$ or 2450 to 2580 cm$^{-1}$ in shift wavenumber with respect to an excitation wavelength is employed as a Raman scattering peak.

6. The measuring method in accordance with claim 4, wherein said enzyme is an oxidoreductase.

7. A measuring method of activity of an enzyme comprising the steps of:

adding ferricyanic ions of a constant concentration and an enzyme of a constant unit to a sample solution containing a target substrate having a known concentration for causing an enzyme reaction;

irradiating said sample solution with an excitation beam of a single wavelength for receiving scattered light from said standard sample solution and separating said scattered light into its spectral components; and measuring a reaction velocity from a time change of peak intensity of reinforced peaks of those of a Raman scattering spectrum from said sample solution before said enzyme reaction, thereby obtaining activity of the enzyme on the basis of said reaction velocity.

8. The measuring method in accordance with claim 7, wherein a peak being present at 1550 to 1680 cm$^{-1}$, 1850 to 1880 cm$^{-1}$, 2000 to 2150 cm$^{-1}$, 2350 to 2380 cm$^{-1}$ or 2450 to 2580 cm$^{-1}$ in shift wavenumber with respect to an excitation wavelength is employed as a Raman scattering peak.

9. The measuring method in accordance with claim 7, wherein said enzyme is an oxidoreductase.

* * * * *